(12) United States Patent
DeCourcy et al.

(10) Patent No.: US 7,414,149 B2
(45) Date of Patent: Aug. 19, 2008

(54) NON-ROUTINE REACTOR SHUTDOWN METHOD

(75) Inventors: Michael Stanley DeCourcy, Houston, TX (US); Nam Quoc Le, Friendswood, TX (US)

(73) Assignee: Rohm and Haas Company, Philadelphia, PA (US)

( * ) Notice: Subject to any disclaimer, the term of this patent is extended or adjusted under 35 U.S.C. 154(b) by 169 days.

(21) Appl. No.: 11/268,152

(22) Filed: Nov. 7, 2005

(65) Prior Publication Data

US 2006/0111575 A1 May 25, 2006

Related U.S. Application Data

(60) Provisional application No. 60/629,989, filed on Nov. 22, 2004.

(51) Int. Cl.
*C07C 51/16* (2006.01)
*C07C 51/21* (2006.01)

(52) U.S. Cl. ..................................... 562/532

(58) Field of Classification Search ................. 562/532
See application file for complete search history.

(56) References Cited

U.S. PATENT DOCUMENTS

| | | | |
|---|---|---|---|
| 3,057,707 A | 10/1962 | Albert et al. | |
| 3,692,823 A | 9/1972 | Gordon | |
| 5,183,936 A | 2/1993 | Etzkorn et al. | |
| 5,426,221 A | 6/1995 | Willersinn | |
| 6,156,921 A | 12/2000 | Wagner et al. | |
| 6,166,248 A | 12/2000 | Heida et al. | |
| 6,281,386 B1 | 8/2001 | Fauconet et al. | |
| 6,300,505 B1 | 10/2001 | Burnett et al. | |
| 6,384,274 B1 * | 5/2002 | Elder et al. | 562/532 |
| 6,596,901 B1 | 7/2003 | Eck et al. | |
| 6,639,106 B1 | 10/2003 | Elder et al. | |
| 2002/0188151 A1 | 12/2002 | Inoue et al. | |
| 2004/0015012 A1 | 1/2004 | Hammon et al. | |

* cited by examiner

*Primary Examiner*—James Wilosn
*Assistant Examiner*—Yevegeny Valenrod
(74) *Attorney, Agent, or Firm*—Marcella M. Bodner

(57) ABSTRACT

The non-routine (e.g., emergency) shutdown of a chemical reaction process is achieved by a method of safely operating a chemical reaction process which comprises the steps of detecting an undesirable condition capable of affecting the process, minimizing the reaction of the reactants, and maintaining a flow of materials through the reaction zones of the process such that the reaction mixture is displaced from the reaction zones. The flow of materials may be maintained for a period of time such that the substantially all of the reaction mixture is displaced from the reaction zones, thereby flushing the reaction zones. The reaction mixture may then be purged to an ancillary vessel, such as an absorber.

12 Claims, 2 Drawing Sheets

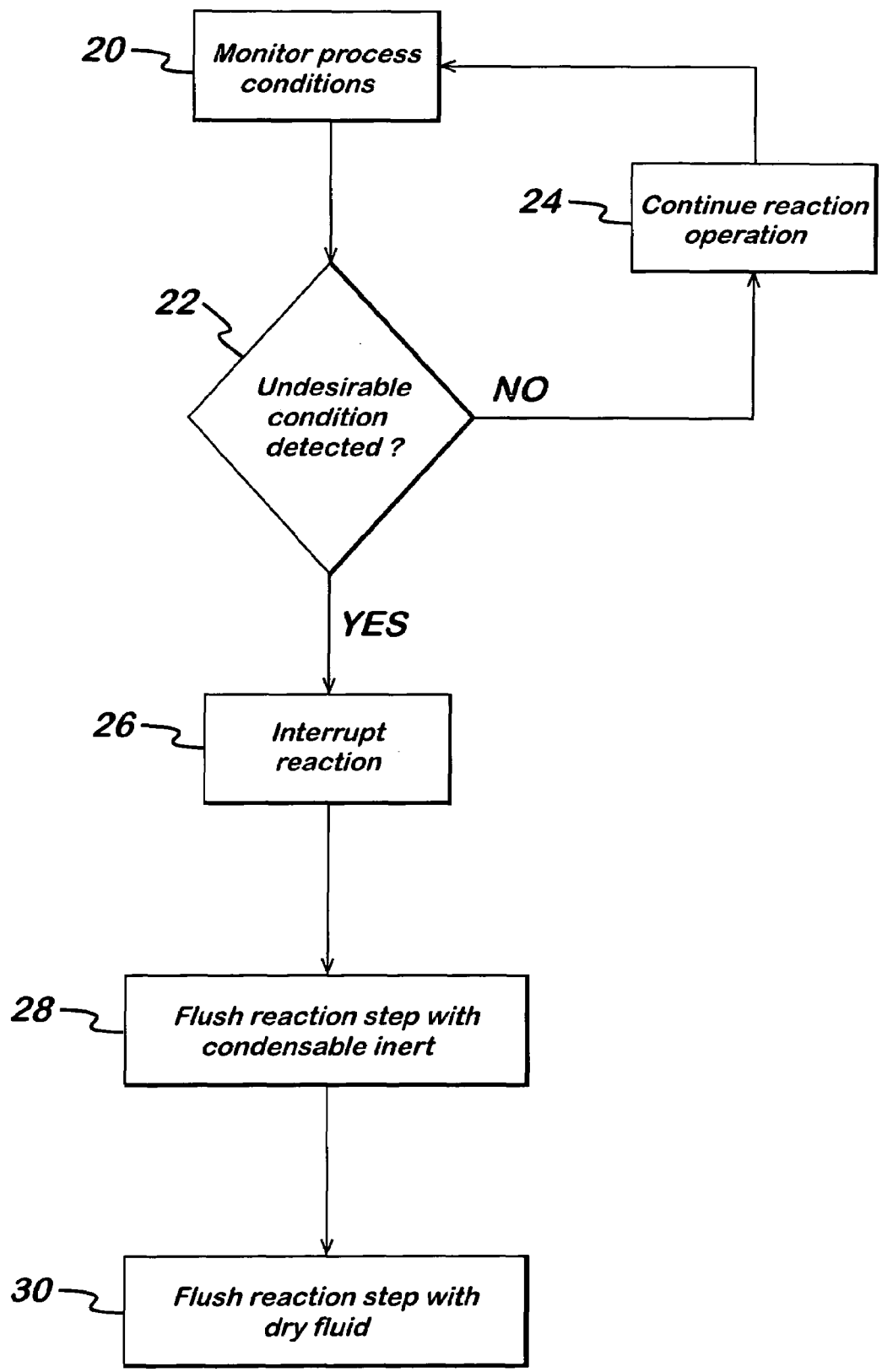

Figure 1:
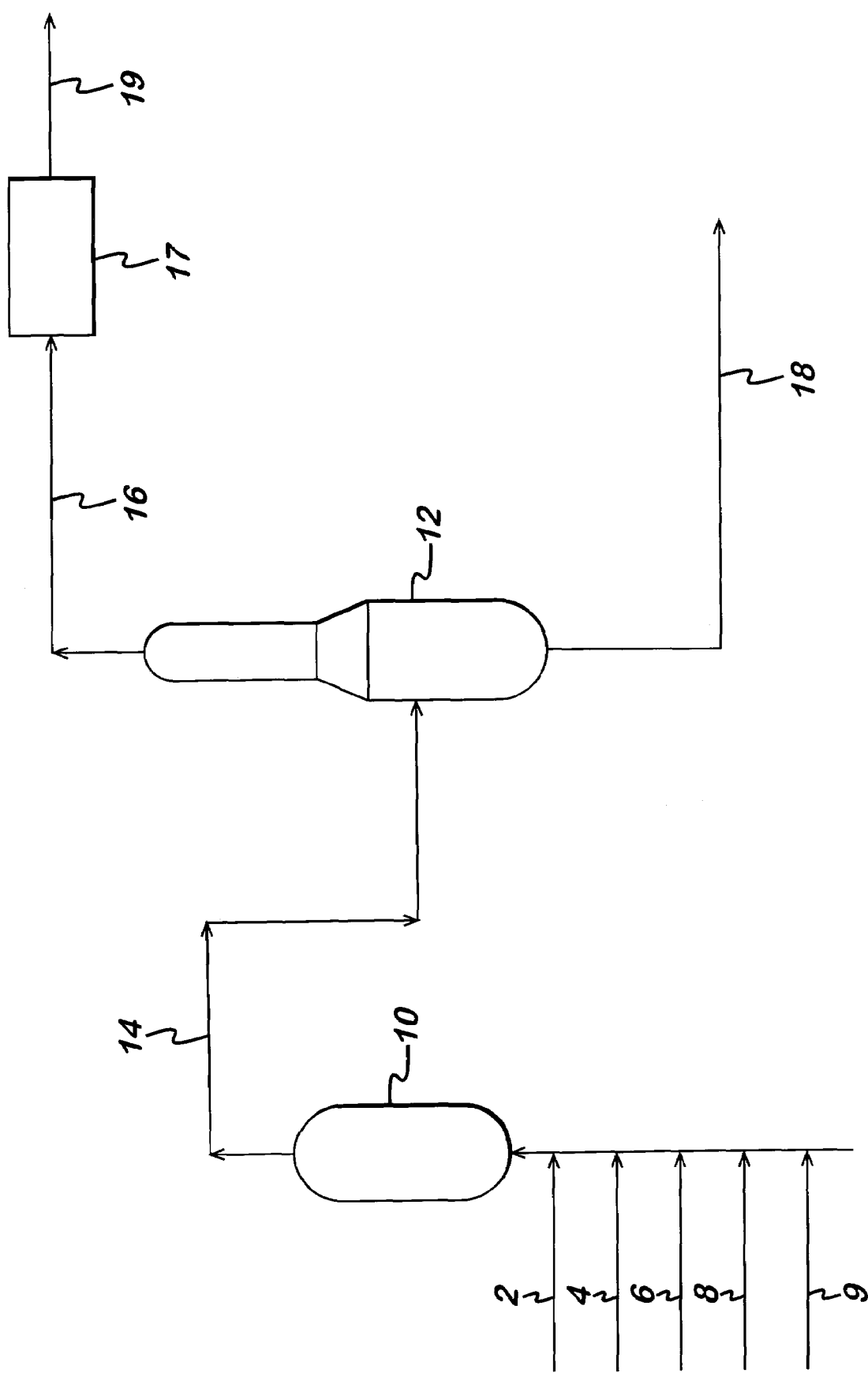

NON-ROUTINE REACTOR SHUTDOWN METHOD

CROSS REFERENCE TO RELATED PATENT APPLICATIONS

This is a non-provisional patent application of co-pending U.S. provisional patent application Ser. No. 60/629,989 filed Nov. 22, 2004.

The present invention is related to a method of operating chemical process hardware during an emergency shutdown situation, more specifically the present invention relates to a method for monitoring partial oxidation reaction processes and for safely shutting down the reaction process when required.

Chemical processes for the production of oxidation products, such as carboxylic acids, anhydrides, nitrites, and alkene oxides are well known. At the heart of these chemical processes are partial oxidation reaction processes comprising catalytic oxidation reactors, where conditions such as temperature, pressure, and reaction rates can be controlled. These reaction processes generally involve providing raw materials, such as a mixture of reactive hydrocarbons and oxygen, to one or more reaction zones contained in a reactor apparatus. Each reaction zone contains one or more catalysts capable of catalyzing the oxidation of the reactive hydrocarbons to various oxidation products in a continuous reaction. Such processes typically produce a mixed product comprising one or more desired oxidation products, unreacted raw materials and one or more reaction by-products. The chemical process, therefore, also often include means for separating and collecting the oxidation products from the mixed product, as well as means for disposing of the waste components. Oxidation reactors may take a number of different forms. For example, some of the well known types of reactors include, but are not limited to, batch reactors, stirred tank reactors, continuous stirred tank reactors (CSTRs), tubular reactors, shell and multiple contact tube heat exchanger reactors, multiple-pass reactors, fixed bed reactors, fluidized bed reactors, and spouted bed reactors. Of these, the shell and multiple contact tube heat exchanger type of reactor is one type that is commonly selected for use in commercial scale partial oxidation processes.

An example of a shell and multiple contact tube heat exchanger reactor of the type commonly used in partial oxidation processes is illustrated in U.S. Pat. No. 6,384,274. Here propylene is oxidized within the reactor to form acrolein, and the acrolein is subsequently further oxidized to produce acrylic acid. The chemical process described in U.S. '274 also includes an absorber which is located downstream of the reactor and which separates and collects the oxidation products as an aqueous solution.

The reactive portion of a partial oxidation process need not be limited to a single reactor and may, instead, comprise two or more reactors. Such an arrangement is disclosed, for example, in U.S. Pat. No. 6,639,106, which describes a process having first and second reactors to perform the 2-stage conversion of propylene to acrylic acid, with acrolein as the intermediate product. In U.S. '106, the product effluent of the first reactor, containing acrolein, is cooled with a heat exchanger before passing onto the second reactor, in which the acrolein is converted to acrylic acid. The process described in U.S. '106 also includes an absorber, positioned downstream of the second reactor, in which the oxidation product is separated from a mixed product effluent of the second reactor, whereby an aqueous solution containing the oxidation product (acrylic acid) is produced.

Constant monitoring and control of chemical oxidation processes, such as partial oxidation processes and the associated downstream processes, are required to avoid equipment damage, personal injury, and accidental releases of chemicals to the environment. Certain undesirable conditions can occur that are capable of affecting the chemical reaction process and may require the immediate shutdown of the chemical reaction process in order to ensure the safety and environmental compliance of the chemical process. These undesirable conditions include flammability in the reactor, loss or malfunction of downstream emissions abatement equipment, lack of containment of the reaction mixture (such as a leak in or around the reactor), a runaway reaction, an undesirable condition in the associated downstream process (e.g., loss of absorbent flow to the absorber), or any other condition or event that might affect the safe control, operation, or monitoring of the reactor and other apparatus used in the chemical reaction process.

Potential causes of unsafe operating conditions include, but are not limited to, contamination of the reactor contents, addition of excess amounts of reagents (such as, for example, due to faulty instrumentation or human error), and loss of reactor cooling. Since some chemical reactions, such as oxidation reactions, are highly exothermic, when the ability to cool the reactor is lost or diminished, the rate of heat generation by the chemical reaction can quickly exceed the rate of heat removal, and the temperature of the reaction mixture rapidly increases. This, in turn, increases the reaction rate and leads to an even higher heat generation rate. The resulting high temperatures inside the reactor can lead to catalyst damage and increased operating pressures. Sustained high temperatures and operating pressures can eventually lead to mechanical failures, fires, explosions, and ultimately the destruction or inoperability of the chemical reaction process and apparatus.

To mitigate the consequences of excessive temperatures and pressures, reaction processes may be outfitted with an emergency relief valve system. When the process reaches a predetermined maximum set point pressure or temperature, such systems typically allow at least a portion of the reaction mixture to be discharged from the reactor. Although this approach may protect the process equipment from catastrophic damage, it also creates a secondary hazard, specifically, the undesirable release of chemicals to the environment.

Chemical processes may also utilize advanced control systems that measure the temperature, pressure, flow and other fluid properties and characteristics to help detect an undesirable condition within the reaction process. Early warning of an undesirable condition can enable plant operators to adopt the necessary counter-measures to return to safe operating conditions.

One example of an early warning system can be found in Hammon et al., U.S. Patent Application Publication Number 2004/0015012 where data from an explosion diagram of the reactor feed gas mixture is digitally stored within a process control system. The explosion data is used to anticipate when the reaction mixture may be approaching a potentially explosive composition. Being alerted to the possibility of an explosive reaction mixture, the process control system can then stop feed flows to the reactor. Due to various practical limitations, however, such as the rate of change of the process conditions and measurement tolerances, the rapid termination of feed flows to the reaction process may not be sufficient to prevent the reaction mixture from actually becoming flammable or explosive. Thus, the potential for arriving at an unsafe condition within the reaction process still exists. Given this possibility, one of the drawbacks of simply terminating flow to the reactor is tat a potentially explosive mixture may be trapped within the reactor. Such a result does not eliminate the hazardous condition and still leaves the possibility that the reactor could ignite or explode.

Terminating flow to the reactor would also be an inappropriate response to other undesirable conditions, such as for example loss of reactor containment (e.g., reactor leak), or a runaway reaction within the reaction process. This means that the same response cannot be used for multiple shutdown scenarios and so the complexity of the operation is increased.

While early warning systems are indispensable, there remains a continued need for improved, decisive and effective non-routine shutdown methods that can be implemented in the event of the development of an undesirable process condition in a chemical reaction process, such as, but not limited to, partial oxidation processes. Thus, chemical manufacturers would welcome the advent of a method that both mitigates undesired conditions in a chemical reaction process and also avoids the creation of secondary hazards, such as environmental releases. Chemical manufacturers would also benefit from the development of a shutdown method that is effective in addressing multiple shutdown scenarios, such that process complexity can be minimized.

The present invention provides a method of safely operating a chemical reaction process. The process comprises providing one or more raw materials selected from the group consisting of a reactive hydrocarbon, an oxidant and a diluent material, to at least one reaction zone, wherein the one or more raw materials form a reactive mixture; and reacting the reactive hydrocarbon with the oxidant, in the at least one reaction zone, to form a mixed product comprising at least one reaction product. The method of safely operating such a chemical reaction process comprises: (a) detecting the existence of an undesirable condition capable of affecting the chemical reaction process; (b) minimizing the reacting of the reactive hydrocarbon with the oxidant; and (c) maintaining a flow of materials through the at least one reaction zone such that at least a portion of the reaction mixture is displaced from the at least one reaction zone.

The step of minimizing the reacting of the reactive hydrocarbon with the oxidant may be performed by adjusting the composition of the reaction mixture by taking at least one action selected from the group consisting of: reducing the flow of reactive hydrocarbon to the at least one reaction zone, reducing the flow of oxidant to the at least one reaction zone, increasing the flow of diluent materials to the at least one reaction zone, providing an inert material to one or more of said at least one reaction zone. The inert material is selected from the group consisting of nitrogen, nitric oxide, nitrous oxide, absorber off gas, steam, carbon dioxide, carbon monoxide, non-reactive hydrocarbons, noble gases, and abatement effluent. Alternatively, the inert material is selected from the group consisting of a dry fluid, a condensable inert, and a combination of a dry fluid and a condensable inert.

The step of maintaining a flow of materials through the at least one reaction zone is performed by taking at least one action selected from the group consisting of: maintaining the flow of diluent materials, increasing the flow of diluent materials, and providing an inert material to one or more of said at least one reaction zone. In a particular embodiment, the step of maintaining a flow of materials through the at least one reaction zone may be performed for a period of time sufficient to displace substantially all of the reaction mixture from the reaction zones, thereby flushing the reaction zones.

The chemical reaction process may be, for example, a catalytic partial oxidation process for producing at least one product selected from group consisting of: (meth)acrolein, (meth)acrylic acid, propylene oxide, ethylene oxide, methyl methacrylate, and maleic anhydride.

In another embodiment of the present invention, where the mixed product of the chemical reaction process further comprises unreacted raw materials and reaction by-products, and the chemical reaction process further comprises the step of separating the at least one reaction product from the mixed product in at least one separation apparatus, the method of safely operating the chemical reaction process further comprising the step of (d) conducting the displaced reaction mixture to the at least one separation apparatus.

The method of the present invention may further comprise the step of (e) minimizing the escape of displaced reaction mixture from the at least one separation apparatus by providing a condensable inert material to one or more of the at least one reaction zone and condensing the condensable inert material after the condensable inert material exits the at least one reaction zone.

One or more steps of the present invention (such as, steps (a), (b), and (c)) may be performed using a computer system, which may, for example, comprise a distributive control system (DCS) capable of performing one or more of steps (a), (b), and (c).

In still another particular embodiment of the method of the present invention, the existence of an undesirable condition is detected, the step of minimizing the reacting of the reactive hydrocarbon with the oxidant is performed by reducing the flow of reactive hydrocarbon and reducing the flow of oxidant to the at least one reaction zone; maintaining the flow of materials by providing a condensable inert material to the at least one reaction zone; maintaining the flow of the condensable inert material until the reacting of the reactive hydrocarbon and oxidant has substantially ceased and the majority of the reactive mixture has been displaced from the at least one reaction zone; and wherein the method of safely operating the chemical reaction process further comprises the steps of: (d) ceasing the flow of condensable inert to the reactor; and (e) providing a second inert material comprising a dry fluid to the at least one reaction zone after a substantial amount of the flow of the condensable inert material to the at least one reaction zone has ceased.

Other and further features and advantages will become apparent from the following detailed description of various embodiments of the present invention, considered in conjunction with the accompanying drawings, in which like reference numbers indicate like features, and wherein:

FIG. 1 is a schematic representation of a chemical process which comprises reaction zones and separation apparatus and which may benefit from the method of the present invention; and FIG. 2 is a flowchart representing an embodiment of the method of the present invention.

One embodiment of the present invention provides a method for safely operating a chemical reaction process, such as a catalytic partial oxidation process. More particularly, FIG. 1 shows a chemical reaction process which may benefit from the method of the present invention and which comprises a reacting means, such as a reactor apparatus 10 containing at least one reaction zone, a separation means, such as a separation apparatus 12, and a waste abatement means, such as a waste abatement apparatus 17.

In one embodiment of the present invention, for example, the reaction apparatus 10 comprises at least one reaction zone, to which raw materials are provided. For example, in the process of FIG. 1, a reactive hydrocarbon, an oxidant and a diluent material are provided via one or more raw material feed streams, for example streams 2, 4 shown in FIG. 1. One or more of the raw materials (i.e., a reactive hydrocarbon, an oxidant and a diluent material) may be mixed prior to feeding to the reaction zone(s), or not. As will be explained in detail hereinafter, an optional condensable inert stream 8, and an optional recycle stream 9 may also be provided to the reaction zone(s).

The at least one reactor may be comprised of a single unit or two or more units in tandem (not shown), and may optionally further comprise intercooler exchangers (not shown) between the tandem units. Additionally, the one or more reactors may comprise one or more catalysts capable of catalyzing the reaction of the selected reactive hydrocarbon to produce the desired reaction products. For example, mixed metal oxide (MMO) catalysts are often used in industry for partial oxidation reactions wherein alkanes and alkenes, such as propane and propylene, are converted to unsaturated carboxylic acids and unsaturated nitriles. Examples of MMO catalysts suitable for use in partial oxidation reactions include but are not limited to: catalysts comprising molybdenum, bismuth, and iron; catalysts comprising molybdenum and vanadium, and catalysts comprising vanadium and phosphorous. Such catalysts are well known in the art and many are commercially available.

The "reactive hydrocarbon" may be any hydrocarbon capable of reacting with oxygen when subjected to the conditions of the chemical reaction process, for example, reaction temperature, reaction pressure, and the presence of catalyst materials, to produce one or more desired reaction products. As used herein, the term "hydrocarbon" includes any and all compounds which contain carbon and hydrogen, and which may also include for example, without limitation, one or more of sulfur, nitrogen, oxygen and chlorine.

The term "diluent material" as used herein means any material that is typically substantially unreactive when subjected to the conditions of the chemical reaction process, for example, reaction temperature, reaction pressure, and the presence of catalyst materials. Diluent materials are often used to minimize the risk of flammability of the reaction mixture and may include, without limitation, carbon monoxide, carbon dioxide, nitrogen, steam, noble gases, etc.

The raw materials mix and combine in the reaction zones to form a reaction mixture, which will undergo reaction when the reaction mixture composition is in a reactive range, and the reaction mixture is subjected to the suitable combination of pressure and temperature. It is well within the capabilities of those skilled in the art to determine the composition and conditions of a reactive reaction mixture as described herein.

Suitable oxidants used in chemical reaction processes may be any composition comprising oxygen. Examples include, but are not limited to, molecular oxygen, air, oxygen-enriched air, ozone, or any mixture of an inert fluid with from 0.1 to 100 volume % oxygen. Examples of inert fluids suitable for mixing with the oxygen include one or more selected from the group consisting of: nitrogen, carbon monoxide, carbon dioxide, argon, neon, helium, and steam.

With regard to optional dry fluid stream 6, the term "dry" as used herein refers to a stream composition with low water vapor content. Specifically, for the purposes of practical application of the inventive method, the term "low water vapor content" means a stream either having a dewpoint of not greater than 32° F. (0° C.), having a dewpoint of not greater than 0° F. (−18° C.), or optionally having a dewpoint of not greater than −20° F. (−29° C.). Dry fluids are particularly advantageous in displacing water vapor from the reaction process and are, therefore, preferred for this purpose when MMO catalysts, which are sensitive to liquid water, are present in the reaction process.

In one embodiment, dry fluid stream 6 may comprise a hydrocarbon that is substantially non-reactive in the reaction process; for example, in a reaction process wherein propylene is oxidized to acrylic acid in the presence of one or more commercially available molybdenum-oxide based MMO catalysts, propane is generally understood to be a non-reactive constituent. With regard to the present invention, a non-reactive constituent or compound is one that is not reactive within the reactor apparatus 10 and thus does not promote or perpetuate a chemical reaction when combined with the reactor apparatus 10. Furthermore, non-reactive constituents will not become reactive even when the reactor apparatus 10 experiences excursions in its operating conditions or when the amount or type of reactive components of the reactor apparatus 10 is altered.

In <another embodiment, dry fluid stream 6 may comprise a non-flammable constituent, such as for example nitrogen or a noble gas. The use of non-flammable dry fluids provides an additional safeguard against combustion of any flammable residues, such as coke or heavy hydrocarbons, which may remain within the reactor apparatus 10 following a shutdown.

In some embodiments, dry fluid stream 6 may comprise an otherwise inert material, or catalyst regeneration element, which re-activates one or more of the catalyst materials in the reaction zones upon contact with the catalyst material. This re-activation may be by chemical oxidation or chemical reduction of the catalytic metals, and serves to improve the catalyst material's efficiency, thereby partially recovering its yield performance. Examples of a catalyst regeneration element that may improve catalyst efficiency include, but are not limited to, nitric oxide, nitrous oxide, air, hot air, and vapor phase phosphorus-containing agents. For example, when the reaction zones of the reactor apparatus 10 comprise a vanadium-phosphorous-oxygen catalyst for oxidizing a hydrocarbon having at least four carbon atoms in a straight chain to produce maleic anhydride, a dry gas feed comprising vaporized trimethyl phosphate may be used for dry fluid stream 6. In this embodiment, the activity of the vanadium-phosphorous-oxygen catalyst material is improved as a result of the exposure to trimethyl phosphate. In addition, when reaction zones of the reactor apparatus 10 comprise one or more commercially available molybdenum-oxide NIMO catalysts for oxidizing propylene to produce acrolein and/or acrylic acid, a dry feed comprising air at a temperature of between 250° C. and 550° C. is used for dry fluid stream 6. In this embodiment, the activity of the molybdenum-oxide MMO catalyst is improved as a result of the exposure to hot oxygen-containing gas.

The condensable inert stream 8 comprises at least one inert component that can be condensed at or close to ambient conditions. As used herein, the term "ambient conditions" is understood to mean at the conditions of 25° C. and 1 atmosphere pressure. Condensable inert stream 8 may comprise a non-flammable constituent, such as, for example, steam. In some embodiments, condensable inert stream 8 may comprise one or more organic constituents that are compatible with the product collection process; examples of such constituents may include methanol, ethanol, butanol, acetone, acetic acid, acrolein, acrylic acid, methacrylic acid, maleic anhydride, ethyl acrylate, butyl acrylate, methyl methacrylate, toluene, methyl isobutyl ketone (MIBK), diphenyl ether, biphenyl, dimethyl phthalate, ditolyl ether, and/or a combination thereof. While the fluid in the condensable inert stream 8 can be provided to the reactor apparatus 10 at any pressure or temperature, the fluid in this line is preferably substantially saturated or superheated to avoid potential condensation when in contact with the catalyst(s) of the reactor apparatus 10.

Recycle stream 9 may comprise one or more streams from elsewhere in the chemical process, provided that it is compatible with the reactor apparatus 10. Compositionally the recycle stream 9 may comprise one or more of reactants, inerts, oxygen, steam, waste gas, effluent from abatement apparatus 17, and mixtures thereof. Recycle stream 9 may be optionally heated before it is returned to the reactor apparatus 10.

The chemical reaction process may be reactions involving total or partial oxidation of organic compounds to produce oxidation products. Examples include but are not limited to: the reaction of propylene to give acrolein and/or acrylic acid (see for example, U.S. Pat. No. 5,426,221; U.S. Pat. No. 5,183,936; U.S. Pat. No. 6,281,386; U.S. Pat. No. 6,166,248; and the above-mentioned U.S. '274, U.S. '106, and U.S. '012; the contents of which are hereby incorporated by reference herein in their entireties); the reaction of propane to give acrolein and/or acrylic acid; the reaction of acrolein to give acrylic acid; the reaction of tert-butanol, isobutene, isobutane, isobutyraldehyde or the methyl ether of tert-butanol (MTBE) to give methacrolein, methacrylic acid, and/or methyl methacrylate (see for example, U.S. Pat. No. 6,596,901; U.S. Patent Application No. 2002/0188151); the reaction of methacrolein to give methacrylic acid; and the reaction of butadiene, n-butane, or other hydrocarbons having at least four carbon atoms in a straight chain to give maleic anhydride (see for example, U.S. Pat. No. 6,300,505; JP 2000/239268).

As shown in FIG. 1, the reaction effluent stream contains a mixed product 14 comprising one or more reaction products (such, for example, as oxidation products), as well as unreacted raw materials and reaction by-products. The mixed product 14 exits the reactor apparatus 10 and is conveyed to the separation apparatus 12. The separation apparatus 12 separates the one or more oxidation products from the unreacted raw materials and reaction by-products, producing product stream 18 and a waste stream 16. For example, without limitation, the separation apparatus 12 may be comprised of one or more apparatus including but not limited to, a heat exchanger, an absorption column, a direct condenser, a spray scrubber, a venturi scrubber, a bubble column, or another apparatus having betrickled surfaces. Those of ordinary skill in the art of process design will recognize that operation of the apparatus such as those listed above may require contacting the reaction process effluent, the product stream, and/or the waste gas stream, with one or more absorbents (not shown). Examples of suitable absorbents for use in connection with the separation apparatus 12 include, but are not limited to, water, acrylic acid, methacrylic acid, maleic anhydride, diphenyl ether, biphenyl, dimethyl phthalate, ditolyl ether and mixtures thereof. Additionally, numerous polymerization inhibitors are known in the art, and may be advantageously employed, along with optional oxygen addition, in connection with the separation apparatus 12 to avoid unwanted polymerization of the oxidation product(s).

In one embodiment of the chemical reaction process which is a process to produce acrylic acid, the separation apparatus 12 comprises an absorber column utilizing a liquid absorbent stream (not shown) that is supplied to the upper portion of the absorber column. This liquid absorbent is preferably cooled (not shown). Suitable absorbents for use in this embodiment, for example, include water, diphenyl ether, biphenyl, dimethyl phthalate, ditolyl ether, and mixtures thereof. In this embodiment, the absorbent stream contacts the mixed product 14 which enters the lower portion of the absorber, and the absorbent stream captures a majority of the acrylic acid product, thereby separating the oxidation product (e.g., acrylic acid) from the unreacted products and reaction by-products. The waste gas stream 16, containing unreacted products and reaction by-products, is conducted from the absorber to the waste abatement apparatus 17 for treatment before being released into the atmosphere.

Product stream 18 may, depending on the desired end-use for the oxidation product, be used as-is, or alternatively, product stream 18 may be further purified (not shown) through means known in the art, such as, for example, distillation, extraction, or crystallization, prior to use.

Waste stream 16, comprising waste components (unreacted raw materials and reaction by-products), is fed to the waste abatement apparatus 17. In some embodiments, at least a portion of waste stream 16 may be optionally recycled (not shown) to the reactor apparatus 10 via recycle stream 9. The waste abatement apparatus 17 eliminates harmful constituents from the waste stream 16 prior to discharge into the environment via abatement effluent stream 19. Often, operation of waste abatement apparatus 17 is both required and regulated by governmental entities. Waste abatement apparatus 17 may comprise one or more apparatus including, but not limited to, flares, thermal oxidizers, incinerators, furnaces, catalytic combustion (CCU) units, scrubbers, condensers, carbon absorption beds, sulfuric acid recovery (SAR) units, plasma reactors, selective and non-selective catalytic reduction (SCR/NSCR) units, and wet oxidation systems.

Optionally, the waste abatement means of the chemical reaction process may also include means for energy recovery, such as, for example, waste heat recovery boilers. Additionally, in some embodiments, capital and operating costs may be minimized by sharing one or more of the apparatus included in waste abatement apparatus 17 with another nearby chemical process. For example, the separation means may include two independent separation apparati each of which transfer waste gas streams to a common CCU. The composition of abatement effluent stream 19 will vary, depending on the composition of waste stream 16 and the specific apparatus utilized in the waste abatement apparatus 17; however, abatement effluent stream 19 may comprise one or more selected from the list including nitrogen, oxygen, carbon monoxide, carbon dioxide, water, hydrocarbons, and noble gas. In some embodiments, at least a portion of abatement effluent stream 19 may be optionally recycled (not shown) to the reactor apparatus 10 via recycle stream 9. In some embodiments of waste abatement apparatus 17, two or more effluent streams (not shown) may be produced, such as for example a gaseous effluent stream and an aqueous effluent stream.

An embodiment of the method of the present invention is represented by the flowchart provided in FIG. 2. The method of the present invention can be carried out manually or by the use of a computer, such as, for example, a distributed control system (DCS), where monitoring criteria, set points, and responsive commands are programmed into the computer. It is well within the capabilities of persons of ordinary skill in the art to apply and perform the method of the present invention either manually or with the aid of a computer.

In order to implement the method of the present invention, some preparation work is needed. First, a list is made of undesirable reaction process conditions requiring shutdown of the reactor apparatus 10. Persons of ordinary skill in the art having detailed knowledge of the design and operation of the particular chemical reaction process to which the inventive method is to be applied will easily compile such a list. Common practice in the art involves conducting a structured review to develop this list, such as a Hazard and Operability (HAZOP) Study. One example of an undesirable reaction process condition may be a loss of reactor containment, wherein the reaction mixture leaks to the atmosphere.

Once the undesirable reaction process conditions have been listed, critical process measurements are identified that are indicative of each of the listed undesirable conditions. For each such critical process measurement, an allowable range of values is then determined which can be used to verify that the undesirable condition is not occurring. The types of critical process measurements used may include one or more selected from the list including temperatures, pressures, flows, feed ratios, flammability calculations, and stream compositions (as determined for example by on-line analyzers), as well as the operating status of support equipment within the reactor apparatus 10 (e.g., reactor coolant circulation pumps, reactant feed vaporizers) and operating status of downstream equipment in the separation apparatus 12 and associated equipment, and the waste abatement apparatus 17 and associated equipment. An example of a critical process measurement that would be indicative of the abovementioned reactor leak condition would be the reactor pressure measurement; this measurement may fall outside of its allowable range when the reactor pressure measurement falls below 5 psig (1020 mmHg).

Referring now to FIG. 2, the method of the present invention generally comprises (a) detecting the existence of an undesirable condition capable of affecting the chemical reaction process; (b) minimizing the reacting of the reactive hydrocarbon with the oxidant; and (c) maintaining a flow of materials through the at least one reaction zone such that at least a portion of the reaction mixture is displaced from the at least one reaction zone.

The step of detecting the existence of an undesirable condition typically involves a first step 20 of monitoring the reaction process conditions and a second step 22 of comparing the critical process measurement values collected in step 20 with their respective allowable ranges as determined by a person of ordinary skill in the art depending upon the specifics of the chemical reaction process. The first step 20 of monitoring the reaction process conditions may be accomplished by gathering all of the values from each of the critical process measurements. The step of detecting the existence of an undesirable condition also typically involves decision steps 24 and 26.

As represented by step 24, if the critical process measurement values are within their allowable ranges, it is determined that no undesirable reaction process conditions are detected and reaction process operations may continue normally, and the first step 20 of monitoring continues. The method provides the greatest benefit if the monitoring and comparison steps are performed frequently. Therefore, if the method of the present invention is to be performed manually, it is recommended that the first monitoring step 20 and the second comparison step 22 are repeated at least once every 30 minutes. If the method of the present invention is to be performed automatically (e.g., via process control computer), it is recommended that the first monitoring step 20 and the second comparison step 22 be repeated at least once every 15 minutes and optionally, the monitoring can occur at least once every five minutes, or at least once every minute, or even at least once every 15 seconds.

When the critical process measurement values fall outside their allowable ranges, an undesirable reaction process condition is detected and action must be taken in accordance with the method of the present invention to shut down the reactor apparatus 10.

As shown in step 26, when an undesirable condition is detected, the reacting of the reactive hydrocarbon with the oxidant is minimized (i.e., interrupted) and a flow of materials through the at least one reaction zone is maintained such that at least a portion of the reaction mixture is displaced from the at least one reaction zone. To minimize/interrupt the reacting of the reactive hydrocarbon with the oxidant, the operating conditions of the reactor apparatus 10 are adjusted such that the reacting of the reactive hydrocarbon and the oxidant is minimized. For example, the flow of the reactor coolant may be significantly increased thereby significantly decreasing the temperature of the reaction zones until the reaction is slowed or halted. In addition, the composition of the reactive mixture in the reaction zones may be adjusted such that the reaction is slowed or even halted, for example, by decreasing the flow (even to the point of terminating the flow) of the reactive hydrocarbons or the oxidants to the reaction zones of the reactor apparatus 10, or by increasing the flow a diluent material to the reaction zones of the reactor apparatus 10. In addition, diluent materials may also be the dry fluid of dry fluid stream 6, the condensable inert materials of condensable inert stream 8, constituents of the recycle stream 9, some other stream containing a gas that does not react within the reactor apparatus 10, and combinations thereof. Such adjustments to minimize/interrupt the reaction occurring within the reaction zones of the reactor apparatus 10 can be accomplished either manually or by a programmed control system.

Determination of the best means to minimize or interrupt the reaction for a particular chemical reaction process is well within the ability of one of ordinary skill in the art. In a particular embodiment of the method of the present invention, the reaction zones are flushed by maintaining at least some flow of materials through the reaction zones for a period of time sufficient to displace substantially all of the reaction mixture from the reaction zones. This may, for example and without limitation, be accomplished by providing a condensable inert material to the reaction zones until the entire reaction mixture is displaced from the reaction zones. By maintaining flow of materials through the reaction zones, the potential for reverse flow (i.e., backflow) is minimized. The period of time required to displace substantially all of the reaction mixture from the reaction zones is easily calculable by persons of ordinary skill in the art and will depend primarily, but not necessarily exclusively, on the size of the reactor apparatus and the flow rates of materials used in the reaction process. As a practical matter, maintaining a volumetric flowrate of materials that is equal to or greater than the normal flow rate of one or more of the feed streams, for example, streams 2, 4, 6 and 8 shown in FIG. 1, is expected to be sufficient for this purpose.

As noted previously, heretofore known reaction process shutdown procedures only involve terminating flow of all materials to the reactor apparatus upon the detection of an undesirable condition. This results in a bottling up of the reaction mixture within the reactor apparatus 10. As is known, the conditions within the reactor apparatus 10 may be suitable for the subsequent combustion of its contents thereby possibly allowing an explosion to occur. This bottling up and subsequent explosion would certainly cause substantial property damage with the potential for personal injury. To overcome this shortcoming, one of the many advantages of the present invention involves flushing the contents of the reactor apparatus 10 with inert material in addition to interrupting/minimizing the reacting of the hydrocarbon with the oxidant.

As shown in step 28, to maintain a flow of materials through the at least one reaction zone such that at least a portion of the reaction mixture is displaced from the at least one reaction zone, for example, a condensable inert material may be provided to the reaction zones of the reactor apparatus 10, thus displacing the reaction mixture from the reactor apparatus 10 while concurrently diluting the reaction mixture. Such dilution provides an increased margin of safety if the reaction mixture is or has the potential to become flammable. As shown in FIG. 1, the condensable inert, such as steam, may be provided to the reactor apparatus 10 via condensable inert stream 8. The reaction mixture displaced from the reactor apparatus 10 may be directed to a secondary container, such as a tank, or the separation apparatus 12, where the components of the reaction mixture can be safely stored and maintained until the chemical reaction process is brought under control.

An additional, optional, flushing step 30, wherein a dry fluid is supplied to the reactor, may be performed, to displace the condensable inert material introduced in step 28 from the reactor apparatus 10. The temperature within the reactor apparatus 10 is typically sufficiently high such that the condensable inert will not condense immediately; however, when the condensable inert is displaced into the separation apparatus 12, the mass and temperature of the apparatus can serve as a heat sink to condense the condensable inert material. Condensation can also be promoted by a heat exchanger (not shown) disposed on the reaction process effluent stream 14 or, alternatively, within the separation apparatus 12. One advantage of using a first flush of condensable gas is that, upon condensation of such inert material, its volume will be greatly reduced, thereby maximizing the available volume for reaction mixture containment within the separation apparatus 12, thereby minimizing the escape of displaced reaction mixture from the separation apparatus 12.

It should be pointed out that while steps 26, 28, and 30 are shown in sequential order in FIG. 2, these steps might be performed concurrently, or in an altogether different order. For example, in one instance where an undesirable condition were detected, the method of the present invention could comprise (1) reducing reactant flow to the reactor; (2) reducing the oxidant flow to the reactor; (3) flowing the dry fluid and the condensable inert simultaneously to the reactor. Reducing reactant flow and oxidant flow to the reactor can involve a reduction of any amount of these flows, including a reduction of up to 100% of their respective flows. Optionally, after the reactant and oxidant flows to the reactor are reduced, the dry fluid could be added just prior to addition of the condensable inert. In yet another alternative, the reactant and oxidant flows may be simultaneously reduced and then the condensable inert may be supplied, followed by addition of dry fluid.

As previously stated, the reaction process of the present invention can include many reactions involving oxidation of organic compounds to produce oxidation products. Examples include but are not limited to: the reaction of o-xylene or naphthalene to give phthalic anhydride; the reaction of indanes to give anthraquinone; the reaction of ethylene to give ethylene oxide; the reaction of propylene to give propylene oxide; and the oxidative dehydrogenation (ODH) of hydrocarbons.

Additionally, the term "oxidation" as used herein is also intended to include "ammoxidation" (i.e., oxidation in the presence of ammonia), and so examples of the reaction process of the present invention can further include reactions including but not limited to the ammoxidation reaction of propylene to give acrylonitrile; the ammoxidation reaction of methane to give hydrogen cyanide; and the ammoxidation reaction of propane to give acrylonitrile.

EXAMPLES

Example 1

In one non-limiting example of the method of the present invention, a list of undesirable reaction process conditions was developed for a catalytic partial oxidation process for producing acrylic acid. In the reaction process of this example, a combined feed of propylene, air, and an inert material (steam) is continuously provided to a shell and multiple-contact-tube reactor and reacted in the presence of one or more commercially-available molybdenum-oxide MMO catalysts, and under process conditions sufficient to oxidize propylene to acrolein and acrylic acid. The list of identified undesirable reaction process conditions includes but is not limited to:

Flammable reactor feed mixture
High reactor pressure
Reaction Process Leak
Runaway reaction/rapidly increasing catalyst temperature
High catalyst temperature
Low catalyst temperature
Incorrect reactant to oxidant feed ratio
Incorrect oxidant to inert ratio
Reactor coolant (salt) pumps not operational
Reactor coolant (salt) tank low level
Incomplete reaction (high acrolein in reaction process effluent)
Fire detected
Liquid Propylene in feed
High pressure in reactor effluent line
Air compressor not operational Critical Process Measurements were then identified for these conditions and allowable ranges for each measurement were identified. Control system software was configured to continuously monitor these critical process measurements in order to identify the occurrence of undesirable reaction process conditions and initiate a reaction process shutdown when needed. When initiated, the reaction process shutdown comprised:

(1) interrupting the oxidation reaction by ceasing air (oxidant) and propylene (reactant) flows while maintaining steam (inert);
(2) displacing the reaction mixture from the reactor with steam (condensable inert) flow
(3) displacing the condensable inert from the reactor with hot air (dry fluid) flow This example shows that the non-routine shutdown method of the present invention is well suited to address many different undesirable reaction process-operating conditions. Thus the method of the present invention provides a safe and environmentally compliant method, with minimal complexity, for addressing the need to shutdown the reaction process.

Example 2

In one non-limiting example of the present invention the reaction process occurred as part of a chemical process for the production of acrylic acid. The chemical process includes two shell-and-tube reactors arranged in series with an associated interstage cooler (herein referred to as a "tandem reactor"), an absorber downstream of the tandem reactor, and a thermal oxidizer that receives overhead flow from the absorber. Each of the shell-and-tube reactor vessels comprise about 10,000 tubes of 1.5" (37.5 mm) diameter that are filled with commercially available molybdenum-oxide (MMO) oxidation catalysts. The volume of the tandem reactor and its associated piping is approximately 5,557 cubic feet (157 cubic meters). The process of this example also includes a computer-based control system capable of sensing undesirable conditions within the chemical process.

Under routine operating conditions, a combined feed of propylene, air and steam is continuously provided to the reaction process under process conditions sufficient to oxidize propylene to acrolein and acrylic acid. As a result of its operation, the tandem reactor contains a reaction mixture comprising propylene, oxygen, nitrogen, acrolein, and acrylic acid; because the extent of reaction varies along the length of the reactor tube, the exact concentrations of components within the reaction mixture varies as well. Thus, the reaction mixture near the outlet of the tandem reactor contains substantially more acrylic acid than the reaction mixture near the inlet end. A reactor outlet stream comprising acrylic acid is continuously removed from the tandem reactor and directed into the absorber, wherein the reactor outlet stream can be contacted with a non-aqueous absorbent, for example but not limited to, biphenyl, diphenyl ether and/or dimethyl ortho-phthalate. A product stream comprising acrylic acid is continuously removed from the bottom of the absorber and a gaseous absorber overhead stream comprising nitrogen and waste components is continuously removed from the top of the absorber. The absorber overhead stream is transferred to a thermal oxidizer wherein the waste components are incinerated and an effluent stream comprising nitrogen and substantially free of waste components is discharged to the atmosphere.

In the scenario of this example, the thermal oxidizer unexpectedly becomes inoperative. In accordance with the requirements of the environmental permit for this chemical process, the occurrence of a non-functioning thermal oxidizer requires shutdown of the reaction apparatus (i.e., minimization/interruption of the reacting of the reactive hydrocarbons and the oxidant). Therefore, the control system, which has been programmed to sense this undesirable condition, reacts in accordance with the inventive shutdown method. The control system interrupts the reaction by terminating the flow of propylene and air to the tandem reactor. However, steam flow to the reactor is maintained during the shutdown. More specifically, steam flow is increased such the tandem reactor is flushed with 75 psig (6 bar) steam at a rate of 60,000 pounds per hour (27,216 kg/hr) for at least a 2 minute duration. This flow rate of steam is sufficient to effectively develop plug flow through the reactor tubes, which is most efficient for purging.

The flow of condensable inert steam causes the reaction mixture to be displaced from the reaction zones of the reactor apparatus and pushed downstream into the absorber apparatus. In accordance with the inventive method, the flow of absorbent is maintained to the absorber during the steam addition, thereby capturing soluble components from the reaction mixture, such as for example acrylic acid, and improving the containment efficiency of the absorber. This optional flow of absorbent also serves to cool the reaction mixture and reduces the potential for combustion, should the displaced reaction mixture be flammable.

After the predetermined amount of steam has been supplied, the steam flow is stopped. A flow of 150 psig (11 bar) of dry nitrogen gas (−80 F/−62 C dewpoint, 99.9%+purity) is subsequently supplied to the reactor at a rate of 5,557 ACFM (157 cubic meters per minute) for a period of at least one minute. This flow rate of nitrogen is sufficient to effectively develop plug flow through the reactor tubes, which is most efficient for flushing. The nitrogen flow causes the steam to be displaced from the reactor and pushed downstream into the absorber. Thus, this nitrogen addition serves to ensure that all steam is purged from the reactor tubes before it can condense, thereby protecting the catalyst from moisture damage. When the steam reaches the absorber, it is condensed and can be drained from the bottom of the absorber. Accordingly, the volume impact of the steam on the absorber is insignificant and the previously purged reaction mixture is not displaced from the absorber. Thus the components of the reaction mixture can remain within the absorber for containment and later remediation. In accordance with the inventive method, the flow of absorbent may optionally be maintained to the absorber during the nitrogen addition, thereby improving the rate of steam condensation within the absorber.

Those skilled in the art will readily understand that, to be able to implement the method of the present invention in a preferred embodiment wherein the reaction mixture is displaced and conveyed from the reaction zones of the reactor apparatus to the absorber apparatus, it would be beneficial to use an absorber apparatus which has a volume that is at least as large as the volume of the reactor, or even at least as large as the volume of the reactor and its associated piping. In such an embodiment, the total volume of the inert material provided to the reaction zones to displace substantially all of the reaction mixture from the reaction zones (i.e., to flush the reaction zones) is less than or equal to the volume of the absorber apparatus. Further, where steam is used as the condensable inert material, it is advantageous for the cooling capacity of the absorber to be able to keep up with the steaming rate to fully condense the steam, it is required that the absorber apparatus have a volume greater than that of the reactor apparatus (or, if desired, greater than the volume of the reactor apparatus and its associated piping). It will also be apparent to one of ordinary skill with the benefit of the present disclosure that the occurrence of a brief delay between the termination of condensable inert (steam) addition and the initiation of the flow of dry fluid (nitrogen) will not substantially detract from the utility of the inventive method. This is because the steam within the reactor tubes will not immediately condense when steam flow ceases. As a practical matter, therefore, it is recommended that the brief delay between these steps should not exceed about 30 minutes.

Implementation of this shutdown method results in the ability to avoid the hazardous conditions associated with "bottling up" the reactor while simultaneously preventing the discharge of unabated emissions to the atmosphere. It is also evident from this example that the shutdown method of the present invention is sufficiently adaptable to address non-routine shutdown scenarios initiated by undesirable conditions occurring outside of the reaction process (for example, an undesirable waste abatement process condition occurring downstream from the reaction).

The present invention described herein, therefore, is well adapted to carry out the objects and attain the ends and advantages mentioned, as well as others inherent therein. While several presently preferred embodiments of the invention have been given for purposes of disclosure, numerous changes in the details of procedures may be made for accomplishing the desired results. For example, the present invention can involve any industrial process having purification of crude (meth)acrylic acid as a part of the process. These and other similar modifications will readily suggest themselves to those skilled in the art, and are intended to be encompassed within the spirit of the present invention disclosed herein and the scope of the appended claims.

What is claimed is:

1. A method of safely operating a chemical reaction process, wherein the process is an oxidation process for producing at least one product selected from group consisting of: (meth)acrolein, (meth)acrylic acid, propylene oxide, ethylene oxide, methyl methacrylate, and maleic anhydride and the process comprises providing one or more raw materials selected from the group consisting of a reactive hydrocarbon, an oxidant and a diluent material, to at least one reaction zone, wherein the one or more raw materials form a reactive mixture having a composition; and reacting the reactive hydrocarbon with the oxidant, in the at least one reaction zone, to form a mixed product comprising at least one reaction product, unreacted raw materials and reaction by-products, wherein the reacting step is selected from the group consisting of: the reaction of propane to produce acrylic acid, the reaction of o-xylene or naphthalene to produce phthalic anhydride, the reaction of indanes to produce anthraquinone, the reaction of propylene to produce acrylic acid, the ammoxidation of propylene to produce acrylonitrile; the ammoxidation of methane to produce hydrogen cyanide; the ammoxidation of propane to produce acrylonitrile, the reaction of isobutene to produce methylmethacrylate, the reaction of MTBE to produce methylmeth-acrylate and the oxidative dehydrogenation (ODH) of hydrocarbons, wherein the chemical reaction process further comprises the step of separating the at least one reaction product from the mixed product in at least one separation apparatus, the method of safely operating the chemical reaction process comprising:

(a) detecting the existence of an undesirable condition capable of affecting the chemical reaction process and selected from the group consisting of: flammability of the reaction mixture, high reactor pressure, cessation of downstream emissions abatement, lack of containment of the reaction mixture, a runaway reaction, rapidly increasing catalyst temperature, high catalyst temperature, low catalyst temperature, incorrect reactant to oxidant feed ratio, incorrect oxidant to inert ratio, reactor coolant system not operational, low level of coolant in the reactant coolant system, an incomplete reaction, fire detected, liquid propylene in feed, high pressure in reactor effluent line, associated air compressor not operational, an undesirable condition in the associated downstream process, and any condition affecting the safe operation of the reaction;

(b) minimizing the reacting of the reactive hydrocarbon with the oxidant;

(c) maintaining a flow of materials through the at least one reaction zone such that at least a portion of the reaction mixture is displaced from the at least one reaction zone, d) conducting the displaced reaction mixture to the at least one separation apparatus; and e) minimizing the escape of displaced reaction mixture from the at least one separation apparatus by providing a condensable inert material to one or more of the at least one reaction zone and condensing the condensable inert material after the condensable inert material exits the at least one reaction zone.

2. The method of claim 1, wherein the step of minimizing the reacting of the reactive hydrocarbon with the oxidant comprises adjusting the composition of the reaction mixture by taking at least one action selected from the group consisting of: reducing the flow of reactive hydrocarbon to the at least one reaction zone, reducing the flow of oxidant to the at least one reaction zone, increasing the flow of diluent materials to the at least one reaction zone, providing an inert material to one or more of said at least one reaction zone.

3. The method of claim 2, wherein said inert material is selected from the group consisting of nitrogen, nitric oxide, nitrous oxide, absorber off gas, steam, carbon dioxide, carbon monoxide, non-reactive hydrocarbons, noble gases, and abatement effluent.

4. The method of claim 2, wherein the inert material is selected from the group consisting of a dry fluid, a condensable inert, and a combination of a dry fluid and a condensable inert.

5. The method of claim 1, wherein the step of maintaining a flow of materials through the at least one reaction zone is performed by taking at least one action selected from the group consisting of: maintaining the flow of diluent materials, increasing the flow of diluent materials, and providing an inert material to one or more of said at least one reaction zone.

6. The method of claim 1, where the step of maintaining a flow of materials through the at least one reaction zone is performed for a period of time sufficient to displace substantially all of the reaction mixture from the reaction zones, thereby flushing the reaction zones.

7. The method of claim 1, wherein the step of detecting the existence of an undesirable condition comprises monitoring one or more process conditions capable of affecting the chemical reaction process using one or more apparatus selected from the group consisting of: an analyzer, a flow meter, a thermocouple, and a pressure indicator.

8. The method of claim 1, wherein one or more of the at least one reaction zone contains at least one catalyst material, said method further comprising the step of regenerating the catalyst and accomplishing one or more of steps (b) and (c), by providing an inert material selected from the group consisting of air, nitric oxide, nitrous oxide, and vapor phase phosphorus-containing material, and mixtures thereof, to one or more of the at least one reaction zone.

9. The method of claim 1, wherein the step of detecting the existence of an undesirable condition comprises determining the composition of the reaction mixture and comparing the composition to pre-existing flammability composition data.

10. The method of claim 1, wherein one or more of steps (a), (b), and (c) are performed using a computer system.

11. The method of claim 10, wherein the computer system comprises a distributive control system (DCS) capable of performing one or more of steps (a), (b), and (c).

12. The method of claim 1, wherein the existence of an undesirable condition is detected, the step of minimizing the reacting of the reactive hydrocarbon with the oxidant is performed by reducing the flow of reactive hydrocarbon and reducing the flow of oxidant to the at least one reaction zone; maintaining the flow of materials by providing a condensable inert material to the at least one reaction zone; maintaining the flow of the condensable inert material until the reacting of the reactive hydrocarbon and oxidant has substantially ceased and the majority of the reactive mixture has been displaced from the at least one reaction zone; and wherein the method of safely operating the chemical reaction process further comprises the steps of:

(f) ceasing the flow of condensable inert to the reactor; and (g) providing a second inert material comprising a dry fluid to the at least one reaction zone after a substantial amount of the flow of the condensable inert material to the at least one reaction zone has ceased.

* * * * *